US010777313B2

(12) United States Patent
Steinhauer et al.

(10) Patent No.: US 10,777,313 B2
(45) Date of Patent: Sep. 15, 2020

(54) ANALYTICS REGARDING VENTILATED PATIENTS (71) Applicant: CareFusion 303, Inc., San Diego, CA (US)

(72) Inventors: Tom Steinhauer, San Diego, CA (US); Terry Lee Blansfield, Orange, CA (US); Leonard Mulkowsky, Del Mar, CA (US); Andres Jesus Calderon, III, San Diego, CA (US)

(73) Assignee: CareFusion 303, Inc., San Diego, CA (US)

(*) Notice: Subject to any disclaimer, the term of this patent is extended or adjusted under 35 U.S.C. 154(b) by 90 days.

(21) Appl. No.: 13/917,614

(22) Filed: Jun. 13, 2013

(65) Prior Publication Data
US 2014/0371618 A1 Dec. 18, 2014

(51) Int. Cl.
G16H 20/17 (2018.01)
A61M 16/00 (2006.01)
(Continued)

(52) U.S. Cl.
CPC ............ *G16H 20/17* (2018.01); *A61M 5/172* (2013.01); *A61M 16/0051* (2013.01);
(Continued)

(58) Field of Classification Search
CPC ...... G06Q 50/22; G06Q 50/24; G06F 19/322; G06F 19/323–327
(Continued)

(56) References Cited

U.S. PATENT DOCUMENTS 4,346,101 A * 8/1982 Lednicer ............. C07D 319/08
514/452
6,148,814 A * 11/2000 Clemmer ............ A61M 16/024
128/200.24
(Continued)

FOREIGN PATENT DOCUMENTS

CN 1493049 A 4/2004
CN 1759398 A 4/2006
(Continued)

OTHER PUBLICATIONS

Girard et al., Efficacy and safety of a paired sedation and ventilator weaning protocol for mechanically ventilated patients in intensive care (Awakening and Breathing Controlled trial): a randomised controlled trial, Jan. 12, 2008, The Lancet, vol. 371, pp. 126-134.*

(Continued)

*Primary Examiner* — Jason S Tiedeman
(74) *Attorney, Agent, or Firm* — Morgan, Lewis & Bockius LLP (57) ABSTRACT A method, system and computer-readable medium are provided for determining compliance with one or more patient care rules and protocols, the method including the steps of sending infusion information from a pump to a processor pertaining to one or more drugs provided to a patient, sending ventilation information from a ventilator to the processor pertaining to ventilation provided to the patient and determining, with the processor, a variation between actual care of the patient and a set of rules and protocols associated with care of the patient at least in part based on the infusion information and the ventilation information.

22 Claims, 6 Drawing Sheets (51) Int. Cl.
*A61M 5/172* (2006.01)
*G06F 19/00* (2018.01)
*G16H 20/10* (2018.01)
*G16H 20/00* (2018.01)
*G16H 40/20* (2018.01)

(52) U.S. Cl.
CPC ....... *A61M 16/021* (2017.08); *G06F 19/3468* (2013.01); *G06F 19/3481* (2013.01); *G16H 20/00* (2018.01); *G16H 20/10* (2018.01); *G06F 19/325* (2013.01); *G16H 40/20* (2018.01)

(58) Field of Classification Search
USPC .......................................................... 705/2, 3
See application file for complete search history.

(56) References Cited

U.S. PATENT DOCUMENTS

| | | | |
|---|---|---|---|
| 2003/0135087 A1* | 7/2003 | Hickle | G06F 19/3456 600/26 |
| 2004/0128162 A1 | 7/2004 | Schlotterbeck et al. | |
| 2004/0129271 A1* | 7/2004 | Hickle | G06F 19/3456 128/204.23 |
| 2005/0177400 A1* | 8/2005 | Rosenfeld | G06F 19/3418 705/3 |
| 2006/0247489 A1 | 11/2006 | Carbis et al. | |
| 2007/0067186 A1 | 3/2007 | Brenner et al. | |
| 2007/0257788 A1 | 11/2007 | Carlson et al. | |
| 2009/0164249 A1* | 6/2009 | Hunt | G06Q 50/22 705/3 |
| 2009/0177181 A1* | 7/2009 | Schmidt | A61M 16/01 604/503 |
| 2010/0121170 A1 | 5/2010 | Rule | |
| 2010/0121654 A1* | 5/2010 | Portnoy | G06Q 10/1093 705/3 |
| 2010/0198622 A1* | 8/2010 | Gajic | G06Q 50/22 705/3 |
| 2010/0261977 A1* | 10/2010 | Seely | A61B 5/0022 600/300 |
| 2010/0268157 A1 | 10/2010 | Wehba et al. | |
| 2010/0324936 A1 | 12/2010 | Vishnubhatla et al. | |
| 2011/0078608 A1* | 3/2011 | Gannon | G06Q 50/22 715/771 |
| 2011/0082440 A1 | 4/2011 | Kimmo et al. | |
| 2011/0184303 A1* | 7/2011 | Skinner | A61B 5/087 600/529 |
| 2011/0213215 A1* | 9/2011 | Doyle | A61B 5/08 600/301 |
| 2011/0257798 A1 | 10/2011 | Ali et al. | |
| 2012/0041279 A1* | 2/2012 | Freeman | A61B 5/0205 600/301 |
| 2013/0006075 A1* | 1/2013 | Baker, Jr. | A61M 16/0051 600/322 |
| 2013/0199533 A1* | 8/2013 | Steinhauer | A61M 16/0057 128/204.23 |
| 2014/0002246 A1* | 1/2014 | Steinhauer | G08C 17/02 340/10.4 |
| 2014/0060540 A1* | 3/2014 | Milne | A61B 5/0205 128/204.23 |
| 2014/0060541 A1* | 3/2014 | Boyer | A61M 16/0051 128/204.23 |
| 2014/0114676 A1* | 4/2014 | Holmes | G06F 19/3456 705/2 |
| 2014/0150796 A1* | 6/2014 | Milne | A61M 16/024 128/205.23 |
| 2014/0235959 A1 | 8/2014 | Jafari et al. | |

FOREIGN PATENT DOCUMENTS

| | | | |
|---|---|---|---|
| EP | 2422695 | A2 | 2/2012 |
| EP | 2609855 | A1 | 7/2013 |
| JP | 2006512673 | A | 4/2006 |
| JP | 2007521849 | A | 8/2007 |
| JP | 2011200472 | A | 10/2011 |
| JP | 2012523895 | A | 10/2012 |
| JP | 2013543769 | A | 12/2013 |
| JP | 2014502854 | A | 2/2014 |
| RU | 2295361 | C2 | 3/2007 |
| RU | 2444281 | C2 | 3/2012 |
| WO | WO-2005050524 | A2 | 6/2005 |
| WO | WO-2005072792 | A1 | 8/2005 |
| WO | WO-2009048462 | A1 | 4/2009 |
| WO | WO-2013/003953 | A1 | 1/2013 |
| WO | WO-2013/067223 | A1 | 5/2013 |
| WO | WO-2013067233 | A1 | 5/2013 |

OTHER PUBLICATIONS

Phyllis Maguire, "Wake Up and Breathe Protocol Cuts Patient Time on the Ventilator," Feb. 2008, http://www.todayshospitalist.com/index.php/index.php?b+articles_read&cnt=511, 3 pgs.
International Search Report and Written Opinion in International Application No. PCT/US2014/039597 dated Oct. 21, 2014, 13 pages.
Nathan Teuscher, "Learn PK/PD, Training for the future, What is a half-life?", Dec. 20, 2010, 4 pages.
International Search Report and Written Opinion for International Application No. PCT/US2014/068922, dated Apr. 2, 2015, 12 pages.
Happ et al., "Wash and Wean: Bathing Patients Undergoing Weaning Trials During Prolonged Mechanical Ventilation", Heart Lung. 2010; 39(6 Suppl), 16 pages.
Chinese Office Action for Application No. 2014800334975, dated Jun. 15, 2017, 10 pages.
Duan, Z., et al., "Comparison Between SmartCare Weaning Mode and Traditional Weaning Mode in the Course of Mechanical Ventilation Weaning", J Clin Res, Sep. 2010, vol. 27, No. 9, pp. 1690-1692.
Chinese Office Action for Application No. 20480033497.5, dated May 2, 2018, 21 pages.
Japanese Office Action for Application No. 2016-519521, dated Mar. 2, 2018, 9 pages.
Russian Office Action for Application No. 2015155889, dated Mar. 19, 2018, 11 pages.
Chinese Office Action for Application No. 201480066337.0, dated Dec. 28, 2017, 11 pages excluding English translation.
Russian Office Action for Application No. 2016127060, dated Jun. 25, 2018, 7 pages.
Chinese Office Action for Application No. 201480066337.0, dated Oct. 15, 2018, 4 pages.
Japanese Office Action for Application No. 2016-519521, dated Oct. 18, 2018, 6 pages.
Japanese Office Action for Application No. 2016-535140, dated Oct. 17, 2018, 7 pages.
Australian Office Action for Application No. 2014278649, dated Feb. 11, 2019, 3 pages.
Chinese Office Action for Application No. 201480033497.5, dated Feb. 3, 2019, 4 pages.
Australian Office Action for Application No. 2014360182, dated May 24, 2019, 3 pages.
European Office Action for Application No. 14819220.6, dated Apr. 8, 2019, 6 pages.
Australian Office Action for Application No. 2014360182, dated Nov. 20, 2019, 4 pages.
Mexican Office Action for Application No. MX/a/2016/006549, dated Jul. 19, 2019, 6 pages.
Japan Office Action for Application No. 2016-519521, dated Feb. 26, 2020, 5 pages.
Japanese Office Action for Application No. 2019-132758, dated May 26, 2020, 7 pages.
European Office Action for Application No. 14819220.6, dated Jul. 2, 2020, 8 pages.

* cited by examiner

ANALYTICS REGARDING VENTILATED PATIENTS

BACKGROUND

Field

The present disclosure generally relates to systems and methods facilitating optimization of patient care, and, in particular, relates to monitoring of ventilated patient sedation, pain therapy and the process of weaning ventilated patients off of the ventilator.

Description of the Related Art

Mechanical ventilator patients, who are intubated in a care facility, typically receive sedation and pain therapy from an infusion pump, as well as life-support from the mechanical ventilator device. Typically, a Nurse operates the infusion pump and has the overall responsibility for the patient. The ventilator is typically operated by a Respiratory Therapist.

The mechanical ventilator provides life support by assisting the patient with the inhalation of oxygen and the exhalation of $CO_2$ in order to maintain the necessary $PaO_2$, $PaCO_2$ and pH arterial blood levels, when the patient is unable to sustain adequate levels with their own spontaneous breathing. Positive pressure mechanical ventilators pump air with a controllable percentage of inspired oxygen (21%-100%) during the inspiratory phase of the breathing cycle. When the inspiratory phase of the breathing cycle is complete, the patient exhales through the ventilator by utilizing the natural recoil characteristics of the lungs. The volume of air that is introduced into the lungs on each cycle is the "tidal volume." This process is very invasive and introduces a high potential for complications such as baro trauma and secondary infections. Furthermore, the analgesics (or other pain medication) and sedatives commonly prescribed to such patients to provide patient comfort can themselves lead to adverse patient outcomes.

Thus, it is desirable to end the use of a mechanical ventilator as early as possible. Many of the rules and protocols for transitioning a patient off of a mechanical ventilator, or "weaning" the patient, include a series of clinical interventions including sedation and pain therapy management where the amount of sedatives and analgesics or other pain medications is reduced to awaken the patient and enable the return of their natural respiratory drive. "Spontaneous awakening trials" or "sedation vacations" where the patient is awakened as tolerated and monitored, and "spontaneous breathing trials" or "weaning trials" where the ventilator support is reduced or stopped for a period of time and the patient is monitored during the trial to identify signs of distress or difficulty. If the patient is able to successfully complete the prescribed weaning trials, "extubation" may be performed where the ventilator is removed, or the patient may be put back on full support to further prepare them for extubation.

Such interventions that facilitate a total dose reduction in analgesic and sedative medications such as the use of nurse controlled protocol guided sedation, the combination of spontaneous awakening and breathing trials, and the use of short acting medications, are associated with improved outcomes such as decreased time of mechanical ventilation and ICU length of stay. Titration of individual patients' sedation throughout their ICU admission is also managed to reduce over-sedation and side-effects, and contributes to reduced duration of mechanical ventilation and length of stay.

SUMMARY

Certain aspects of the disclosed method facilitate managing rules and protocols for ventilator patient care. In certain embodiments, a method is provided for determining compliance with one or more patient care rules and protocols. The method includes the steps of sending infusion information from a pump to a processor pertaining to one or more drugs provided to a patient, receiving ventilation information from a ventilator to the processor pertaining to ventilation provided to the patient and determining, with the processor, a variation between actual care of the patient and a set of rules and protocols associated with care of the patient at least in part based on the infusion information and the ventilation information.

In certain embodiments, a system for determining compliance with one or more patient care rules and protocols is provided. The system comprises an infusion pump providing infusion information pertaining to one or more drugs provided to a patient, a ventilator providing ventilation information pertaining to ventilation provided to the patient and a processor communicably coupled to the infusion pump and the ventilator and configured to determine a variation between actual care of the patient and a set of rules and protocols associated with care of the patient at least in part based on the infusion information and the ventilation information.

In certain embodiments, a non-transitory computer-readable medium having computer-executable instructions stored thereon for execution by a processor to perform a method of determining compliance with one or more patient care rules and protocols is provided. The method comprises the steps of receiving infusion information pertaining to one or more drugs provided to a patient, the one or more drugs including sedatives and pain therapy drugs, receiving ventilation information pertaining to ventilation provided to the patient and providing one or more analytics for display at a client device, the one or more analytics generated at least in part based on the infusion information and the ventilation information, where the one or more analytics provide indications of variation between actual care of the patient and a set of rules and protocols associated with care of the patient.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The process of managing care of a ventilated patient to ensure optimal levels of sedation and pain therapy and proper ventilation to minimize side effects of over sedation or prolonged ventilation is essential to reduce duration of mechanical ventilation and length of stay. To facilitate managing of these concerns, many critical care facilities such as hospitals, intensive care unit ("ICU"), long term acute care ("LTAC"), skilled nursing facility and/or other care facilities, may have one or more rules and protocols, such as best practice rule sets, sedation protocols, ventilation and weaning protocols and other similar guidelines, to guide nursing and medical staff. In one example, one or more patient care rules and protocols are defined and/or communicated according to best practice rule sets, predefined rules and protocols, and/or physician orders for providing care to ventilated patients. As used herein, the phrase "rules and protocols" is used generally to refer to one or more orders (e.g., physician order), best practices, rules and/or protocols for providing care to ventilated patients.

Because following these rules and protocols is intended to lead to optimal results in patient care, it is helpful to facilitate regular oversight of whether these rules and protocols are followed, and provide for management and updating of such rules and protocols. Typically such rules and protocols provide for a set of steps to be followed for each patient placed on a mechanical ventilator with respect to dosage and titration of sedatives and pain therapy medication (e.g., analgesics), timing and frequency of spontaneous awakening trials or sedation vacations ("SATs"), timing and criteria for performing spontaneous breathing trials ("SBTs") and timing and criteria for patient extubation when mechanical ventilation is terminated and the tube is removed from the patient.

These rules and protocols are usually put into place and/or communicated by physicians and/or care facility staff and supervisors to be followed by nurses and therapists. To provide for monitoring and improving compliance with such rules and protocols within a patient care facility or network, embodiments of the disclosed method and system provide for receiving information from one or more systems and machines including the infusion pump administering sedation and pain therapy to the patient, as well as the ventilator providing ventilation to the patient, hospital information system, monitors, laboratory systems and/or pharmacy and dispensing systems. In some embodiments, the information is collected directly from these devices without requiring any interaction from the nurse or therapist and used to generate analytics regarding the different steps of the rules and protocols for weaning a patient off of the ventilator. In addition to the infusion pump and ventilator information, other data may also be collected from other entities, including for example, demographic data regarding the patient as well as patient condition data, and may be used in assessing protocol and best practices compliance. In one example, in response to the information collected from the infusion pump and ventilator, and optionally other mechanisms or entities, one or more analytics may be generated. For example, compliance information may be generated that indicates whether the nurses and/or therapists are taking the right steps in optimal patient care. In one example, one or more markers and/or notifications may be provided to the nurse and/or therapist in response to the collected data.

Measuring and driving compliance may enable clinicians to measurably optimize and improve the ventilator weaning of patients. The data collected can be processed to generate various markers and/or analytics that provide insight into the clinical intervention events and how the timing/pattern of these events affects the weaning process and facilitate a complete view of the weaning process, including sedation/pain therapy, SATs, SBTs and extubation, thus, driving better cross-functional teamwork between physicians, nursing and respiratory technicians.

Figure 1A:
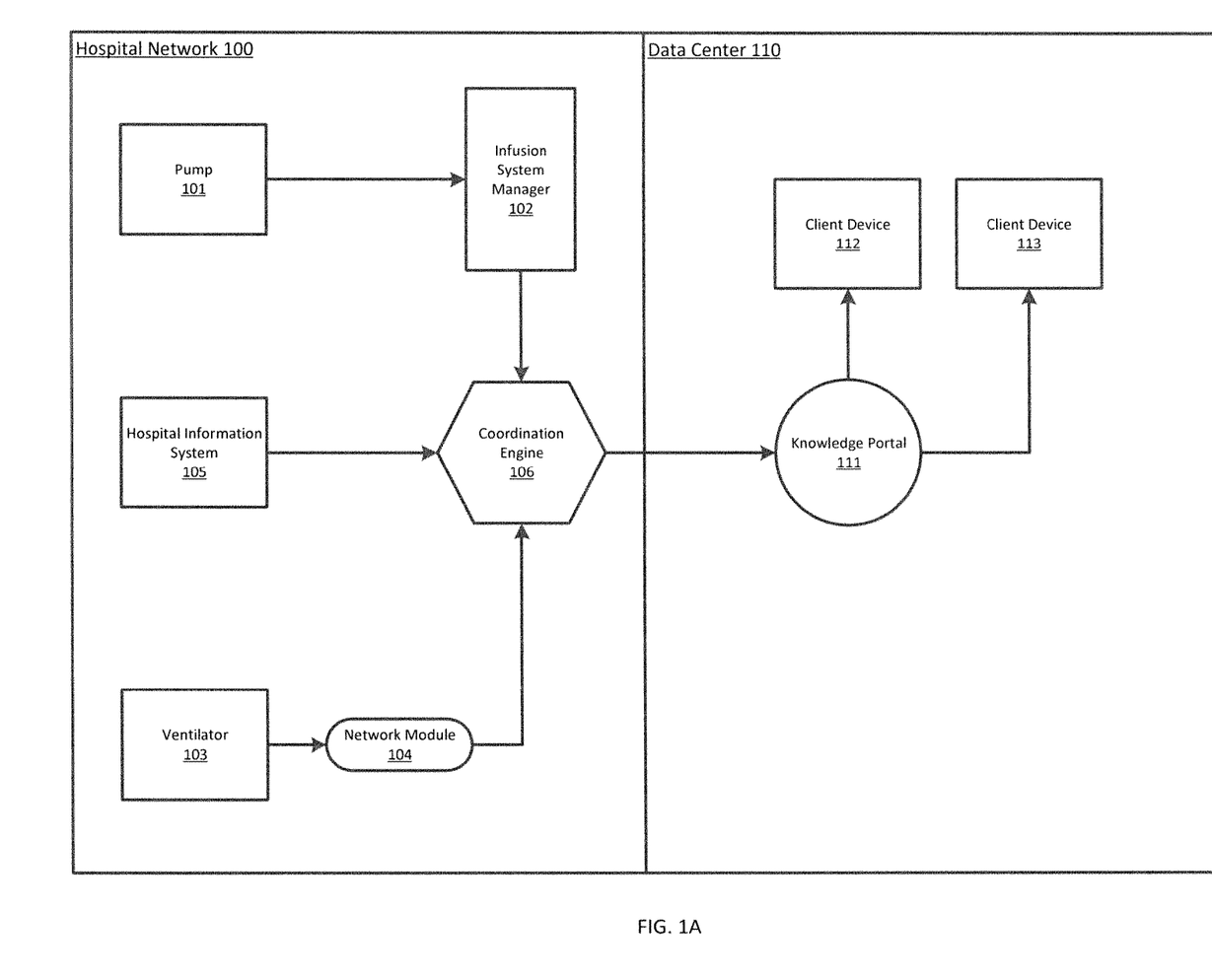
FIGS. 1A and 1B depict exemplary hospital networks for collecting patient information and facilitating management of rules and protocols for ventilator patients in accordance with aspects of the present disclosure.
Figure 1B:
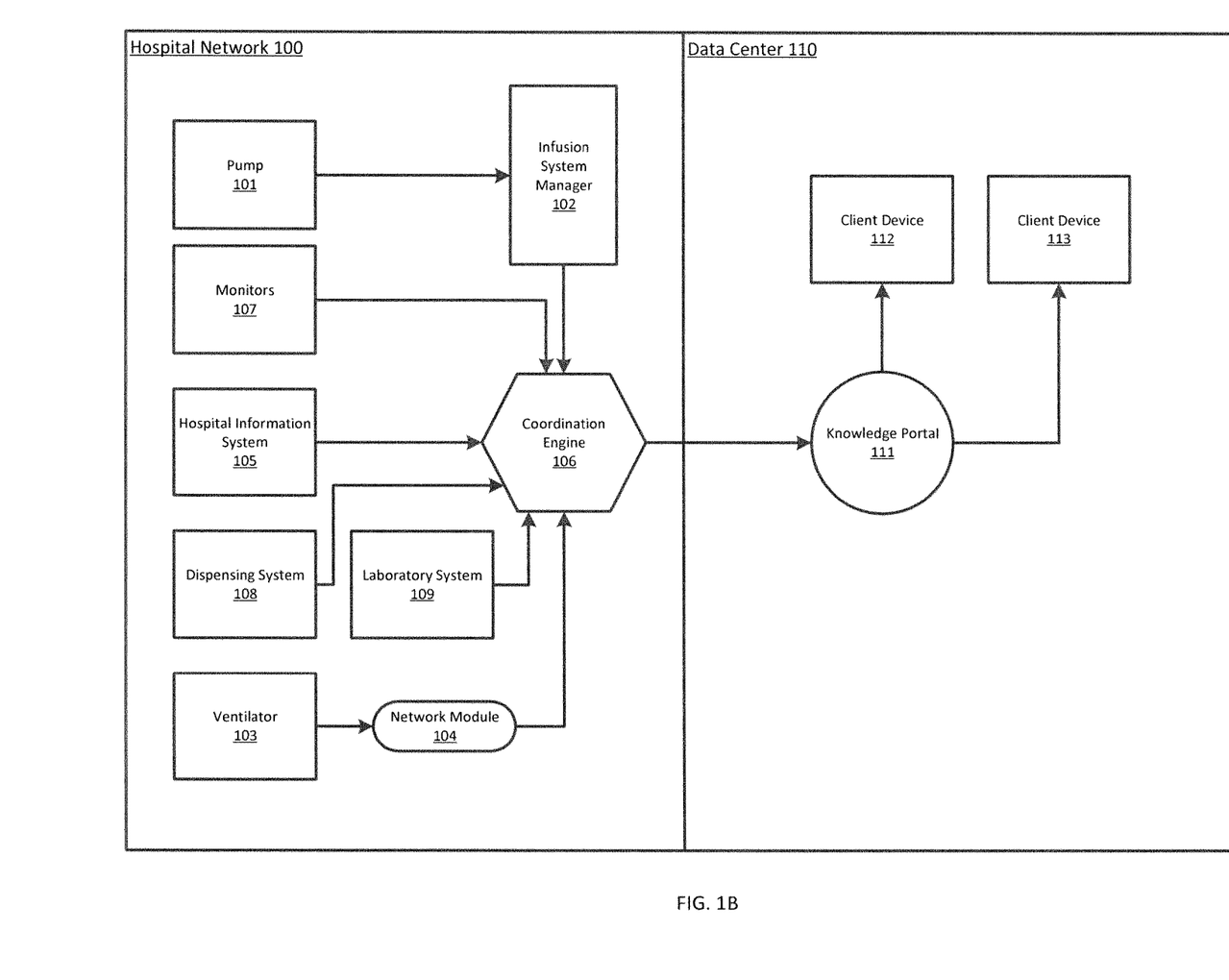

FIGS. 1A and 1B depict an example hospital network 100 for collecting patient information and facilitating management of rules and protocols for ventilator patients. As shown in FIG. 1A, the hospital network 100 includes an infusion pump 101, an infusion system manager 102, a ventilator 103, a network module 104, a hospital information system 105, and a coordination engine 106.

The infusion pump 101 provides sedation and pain therapy to a patient. In one example, the infusion pump 101 represents a collection of one or more infusion pumps for providing medication including pain and/or sedation medication to a patient. In one example, the infusion pump 101 may include one or more channels, and each channel may provide at least one of a sedative or pain medication (e.g., analgesics) to the patient. As described above, the infusion pump is typically operated by a nurse.

The infusion pump 101 is coupled to the infusion system manager 102 and provides infusion messages to the infusion system manager 102. The infusion messages may, for example, indicate start and end times for specific doses/rates of medication administered to the patient. For example, each time the dosage and/or rate of one or more of the medication (e.g., sedatives and/or analgesics) is modified at the pump 101, an infusion message is generated by the pump 101 and sent to the infusion system manager 102. In one example, the pump 101 provides messages regarding the type of medication, dosing of medication and bolus dose patterns of medication administered at the pump 101. The infusion system manager 102 may further receive information regarding the identification of the patient associated with infusion pump 101 from the pump 101 or hospital information system 105. The pump 101 and infusion system manager 102 are depicted as separate elements for exemplary purposes. In some embodiments, the functionality of the infusion system manager 102 may be integrated within an infusion pump 101.

The infusion system manager 102, processes the infusion messages received from the pump 101, and provides infusion information to the coordination engine 106. In one example, the infusion information provided to the coordination engine 106 includes patient identification information (e.g., patient ID), drug information (e.g., drug type), infusion start and/or stop times for each drug, and dose and/or rates for each drug (e.g., continuous infusion dosage, bolus dosage patterns, etc.). The information may be provided for different drugs administered at pump 101, including the sedation and pain therapy medication administered to the patient. The ventilator 103 also provides information to the coordination engine 106 through the network module 104. Ventilation information provided to the coordination engine 106 may include the mode of ventilation, respiratory rate, tidal volume, amount of oxygen, amount of peek respiratory pressure, alarms that are triggered, and/or other ventilation information available at the ventilator 103. In one example, the ventilator 103 may further provide a respiratory rate over tidal volume calculation. The calculation may be the respiratory rate, which represents the number of breaths taken within a set amount of time (e.g., 60 seconds) over the tidal volume, which represents the normal volume of air displaced between normal respiration and expiration when extra effort is not applied. The information from the ventilator 103 is provided to the coordination engine 106 through network module 104. In some examples, the network module 104 may be integrated into the ventilator 103. In one embodiment, the ventilator 103, the network module 104 or a separate element in communication with the ventilator 103 and/or network module 104 may be present within the hospital network and configured to receive and/or process messages from the ventilator 103 before forwarding ventilation information to the coordination engine 106.

The coordination engine 106 may also receive patient "ADT information" from the hospital information system 105. The ADT (admission, discharge, transfer) information may include demographic information as well as patient state information. Patient demographic information may include, for example, patient sex, date of birth, attending, admitting and consulting doctors, location, blood type, height and weight, admit date and time, In/Out patient. Patient state information may include, for example, patient admit, discharge, transfer, registration, information update and other similar information regarding the state of the patient within the care facility.

In one embodiment, coordination engine 106 is embodied in any interface engine or application that aggregates data from one or more devices and systems and sends such data to an analytics application such as the knowledge portal 111. In one example, the coordination engine 106 facilitates processing, filtering and/or transformation of information received from one or more machines and/or system including the infusion system manager 102 and network module 104, for facilitating transferring the data to a respiratory knowledge portal 111 for processing and analysis. In one example, the coordination engine 106 receives the information, processes the information, and generates actionable data items for processing to the knowledge portal 111. In one embodiment, the coordination engine 106 is embodied in a processor. U.S. patent application Ser. No. 13/421,776, entitled "SCALABLE COMMUNICATION SYSTEM," filed on Mar. 15, 2012, and incorporated herein by reference in its entirety, describes an example coordination engine for use with the present disclosure.

The coordination engine 106 is communicably coupled to a respiratory knowledge portal 111 of a data center 110. Data center 110 includes the knowledge portal 110 communicably coupled to one or more client devices 112 and 113. The data center 110 may be located remote from the hospital network 100 or may be part of the hospital network 100. In one example, the coordination engine 106 and knowledge portal 111 may be implemented within a single server or one or more servers communicably coupled to one another. In some examples, the functionalities of the coordination engine 106 and knowledge portal 111 may be performed by a single application or one or more applications collaborating to performing one or more of the functionalities described herein with respect to the coordination engine 106 and knowledge portal 111.

In one example, the knowledge portal 111 receives the infusion information and ventilation information from the coordination engine 106, and processes the information to generate one or more markers and analytics and provide information regarding compliance with patient care rules and protocols. The knowledge portal 111, in some embodiments, is implemented as an application that receives information from one or more devices, such as pump 102 and ventilator 104, within a hospital network 100, and analyzes the data to provide analytics. In one embodiment, the respiratory knowledge portal 111 is embodied in a processor. U.S. patent application Ser. No. 13/756,421 entitled "RESPIRATORY KNOWLEDGE PORTAL", filed on Jan. 31, 2013 and incorporated herein by reference in its entirety, describes an example respiratory knowledge portal for use with the present disclosure.

The knowledge portal 111 may, for example, have access to a set of pre-defined rules and protocols (e.g., best practices). The rules and protocols may be defined based on historical data and/or manually by the care facility or other entity. Using the infusion information and ventilation information received from the coordination engine 106, the knowledge portal 111 can determine one or more markers corresponding to preferences defined by the rules and protocols. The knowledge portal 111 may further be configured to measure variability from the pre-defined rules and protocols and may provide one or more analytics regarding the variance from rules and protocols (e.g., reports, notifications, etc.) to one or more entities (e.g., care facility supervisors, nurse, respiratory therapist, etc.).

In one example, a library (e.g., a drug library) is accessible by the knowledge portal 111. The drug library may include a master drug list that identifies drugs by name and/or an id. In one example, the knowledge portal 111 may further be configured with information regarding the drug type for drugs listed within the master list. For example, for one or more drugs of the master list, the knowledge portal 111 may have access to data identifying the drug type as a pain therapy drug (e.g., analgesics) or a sedative. In one example, the designation of drug types is performed by an entity such as the care facility or other third party entity.

As part of the rules and protocols, the knowledge portal 111 may further be provided with information indicating preferred drugs for a ventilator patient. For example, the rules and protocols may specify preferred pain therapy and sedative drugs for a ventilator patient as well as a preferred dosage and/or dosage ratios for each of the pain therapy and sedatives. In some embodiments, the rules and protocols specify a preferred combination of pain therapy and sedation drugs. The combination of drugs may be specified to ensure the correct combination of specific drugs and/or dosing of those drugs.

Drug preferences may be defined based on patient specific characteristics, and defined per patient or for a group of patients sharing similar characteristics. Patient specific characteristics may include demographic information such as those examples provided herein. The knowledge portal may further have access to information regarding limits (e.g., hard and soft limits) for one or more drugs listed in the master list. In one example, the library includes drug information for each drug including the drug name and identifier, drug type and/or drug limits.

Furthermore, the rules and protocols may include weaning rules and protocols, defining preferences regarding SATs and SBTs including timing, frequency and/or duration of SATs and SBTs, prerequisites to SBTs such as performing an SAT within a predefined period of time, and other patient data that may indicate whether the patient is a good candidate for an SBT and/or weaning (e.g., patient vitals, successful SATs, etc.), and/or rules regarding extubation, including timing of extubation and/or prerequisites such as a successful SBT performed within a specific period of time from the extubation and other patient data that may indicate whether the patient is a good candidate for an SBT and/or weaning (e.g., patient vitals, etc.).

Based on the defined rules and protocols and the information available regarding drugs within the master list, and the infusion information and ventilation information received from the coordination engine 106, the knowledge portal 111 may determine infusion and ventilation analytics.

The infusion and ventilation analytics may provide insight regarding variance from the pre-defined rules and protocols.

FIG. 1B depicts an alternative example hospital network 100 for collecting patient information and facilitating management of rules and protocols for ventilator patients. The hospital network 100 of FIG. 1B is similar to that of FIG. 1B, but depicts additional systems and machines that may provide information used in addition to the infusion information and ventilation information, in generating the analytics at the knowledge portal 111.

As shown, in addition to the elements shown in FIG. 1B, the coordination engine is further coupled to monitors 107 (e.g., vital signs monitors), dispensing system 108 (e.g., a pharmacy system and/or dispensing machine(s)), and laboratory system 109. The coordination engine receives information regarding patient medications, condition and vital signs, from one or more machines and/or systems including, but not limited to, for example, monitors 107, dispensing system 108, and laboratory system 109 (e.g., a pharmacy system). The vital signs and other data may be used by the knowledge portal 111 in various steps of the processes described herein for determining analytics regarding variance from rules and protocols defining best practices, as well as, to provide indicators of when a patient is a good candidate for weaning (e.g., one or more of an SBT or extubation) in addition to various markers and analytics described herein.

In one example, the knowledge portal 111 is coupled to the client devices 112 and 113 and provides the determined metrics and analytics for display at the one or more client devices 112 and 113. In one example, the metrics and analytics may be provided as notifications or warnings to nurses, respiratory technicians or other care providers (e.g., when a deviation from preferred rules and protocols is recognized, or when a preferred event should be performed). In another example, one or more of the markers and analytics may be provided to those in a supervisory role to provide an overall view of the process, identify issues in actual weaning processes and patient care, and provide insight into the pattern of events that lead to optimal results with respect to a patient. The metrics and analytics may be analyzed and provided in real time or near real time for display at the client devices 111. In one example, the analytics may further be used to provide decision support for performing patient care within respect to ventilated patients. In some embodiments, the knowledge portal 111 may provide the metrics and analytics to the client devices 112 and 113 over a wired or wireless network or communication channel.

FIG. 1B depicts another example of hospital network 100. As shown in FIG. 1B, in addition to the infusion information and ventilation information, the analytics generated at the knowledge portal 111 may further be generated based on other machine data providing patient information and vital signs, from one or more machines and/or systems including, but not limited to, for example, monitors 107, dispensing system 108 (e.g., a pharmacy system and/or dispensing machine(s)), and laboratory system 109. The vital signs and other data may be used by the knowledge portal 111 in various steps of the processes described herein for determining analytics regarding variance from rules and protocols defining best practices, as well as, to provide indicators of when a patient is a good candidate for weaning (e.g., one or more of an SBT or extubation) in addition to various markers and analytics described herein.

Figure 2:
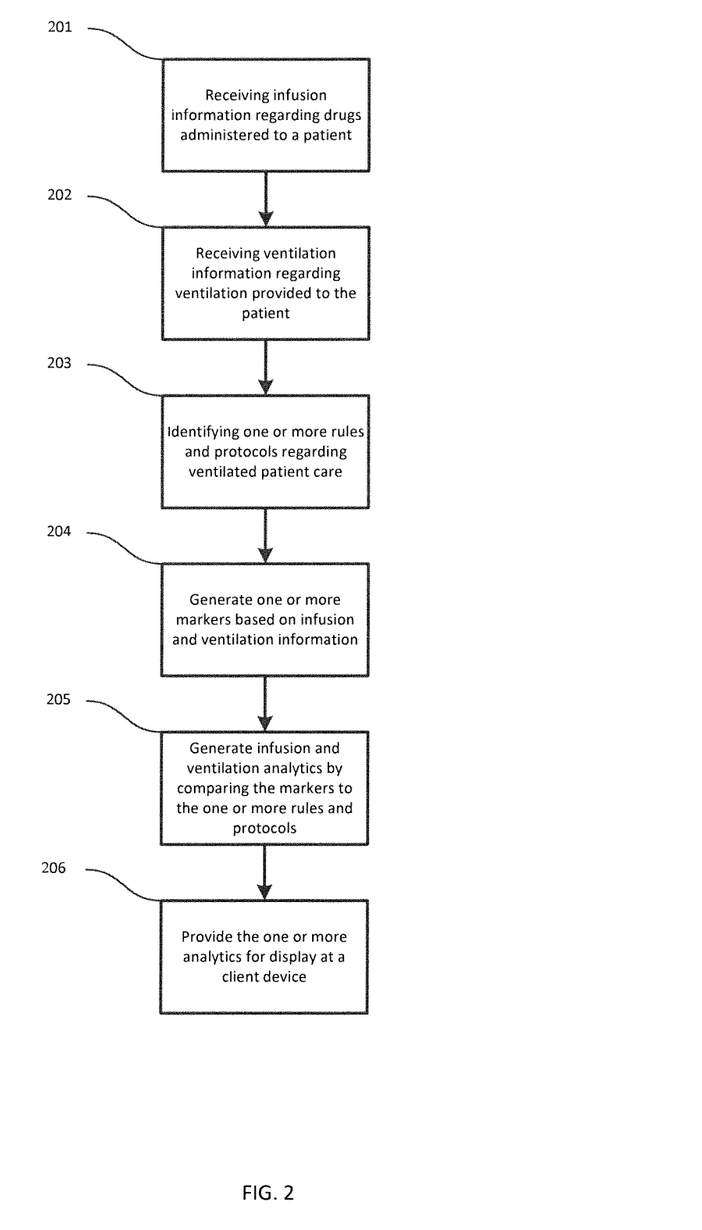
FIG. 2 illustrates an example process for providing information regarding compliance with ventilated patient care rules and protocols.

FIG. 2 illustrates an example process 200 for providing information regarding compliance with ventilated patient care rules and protocols. In step 201, infusion information regarding drugs administered to a patient is received at the knowledge portal 111. The information may be provided from an infusion pump (e.g., infusion pump 101 and/or infusion system manager 103). The information may include patient identification, drug types administered to a patient, drugs dosage and/or rates, as well as infusion start, stop.

In step 202, ventilation information regarding ventilation provided to the patient is received at the knowledge portal 111. The information may be received from a ventilator (e.g., ventilator 103). The information may include the mode of ventilation, respiratory rate, tidal volume, respiratory rate divided by the tidal volume, percent of inspired oxygen (e.g., within a range of 21% to 100%), amount of peek inspiratory pressure, alarms that are triggered, and/or or other ventilation information available at the ventilator. In other embodiments, information is provided from additional systems, as discussed above.

In step 203, one or more rules and protocols regarding ventilated patient care are identified. In one example, the rules and protocols define best practices for weaning patients off of mechanical ventilation. The rules and protocols may be pre-defined by an entity such as the care-facility or other entity having knowledge of best practices.

The rules and protocols identified in step 203 may, for example, include rules and protocols regarding medication or drugs administered to patients. In one example, the information indicates preferred drugs for a ventilator patient. For example, the rules and protocols may specify preferred pain therapy and sedative drugs for a ventilator patient as well as a preferred dosage and/or dosage ratios (e.g., ratio of sedative or pain therapy drugs for each patient) for such drugs. The rules and protocols may further include limits (e.g., soft or hard limits) for one or more drugs administered to a patient. Furthermore, the rules and protocols may include weaning rules and protocols, including rules and protocols regarding SATs, SBTs, and extubation including timing, frequency, duration and/or preceding or following events.

In step 204, one or more markers are calculated according to the information received in steps 201 and 202. In some embodiments, the one or more markers may also be generated based on information received from the hospital information system 105, monitors 107, dispensing system 108 and laboratory system 109. The one or more markers may correspond to desirable values and events defined by the rules and protocols identified in step 203. The one or more markers may, for example, include identification of the drugs administered to a patient, weight-based doses of drugs administered to a patient, information regarding bolus doses, and occurrence and timing of one or more SATs, SBTs and extubation.

In step 205 infusion and ventilation analytics are generated by comparing the one or more markers to the rules and protocols to determine a variance from best practices. For example, the drugs administered to a patient as well as the dosages of the drugs are compared to the rules and protocols to determine if the preferred drugs are administered to a patient at the preferred dosages, and within predefined limits. Furthermore, it is determined whether SATs are administered according to best practice, including timing and frequency of SATs, and whether the SATs are successful based on at least the duration of each SAT. Additionally, it is determined whether SBTs are performed according to the rules and protocols, including whether a patient that is a good candidate for weaning undergoes an SBT and whether prerequisites for an SBT are met, as well as the success of the SBT. Also, it may be determined if extubation of a patient is performed according to the rules and protocols including the timing of the extubation and prerequisites of the extubation being met. An example process for generating infusion analytics is described in further detail below with respect to FIG. 3. An example process for generating ventilation analytics is described in further detail below with respect to FIG. 4.

In step 206, the one or more analytics are provided for display at a client device. In one example, the analytics are provided as notifications to one or more entities such as a nurse or respiratory therapist. In another example, the analytics may be provided in one or more reports to one or more user in a supervisory role.

Figure 3:
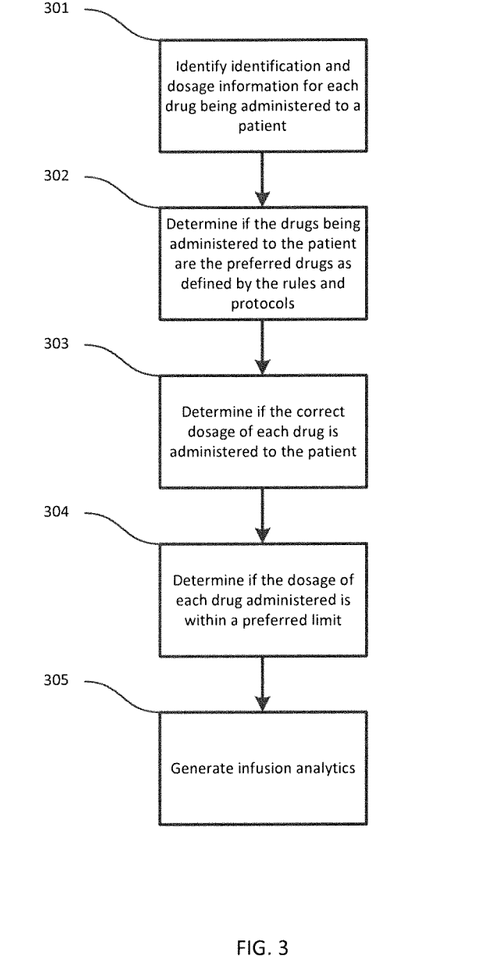
FIG. 3 illustrates an example process for generating example infusion analytics for a ventilated patient.

FIG. 3 illustrates an example process 300 for generating example infusion analytics for a ventilated patient.

In step 301, identification and dosage information for each drug administered to the patient are identified. As described above, with respect to FIG. 2, the identification and dosage information is determined based on information provided by the infusion pump. In one example, a drug library including a master drug list is used to identify drugs by name and/or an id. The infusion pump 101 provides the drug name and/or id for each drug administered to the patient at the infusion pump 101. Dosage information of the drug may be a weight based dosage of each drug administered to the patient calculated according to the dosage information for each drug administered as provided by the infusion pump, and a weight of the patient that is provided as part of the ADT information regarding the patient.

In step 302, it is determined if the drugs administered to the patient are the preferred drugs as defined by the rules and protocols. In one example, the rules and protocols define specific preferred sedative and pain therapy drugs to be administered to the patient. For example, the rules and protocols may specify preferred pain therapy and sedative drugs for a ventilator patient. In one example, the preferences may be defined according to specific patient characteristics. The determination of which drugs are defined as preferred drugs for the patient may be performed by determining specific patient characteristics of the patient and determining the preferred drugs for the patient based on the characteristics.

In step 303, it is determined if the correct dosage of each drug is administered. The rules and protocols may specify preferred dosage and/or dosage ratios for the pain therapy and sedative drugs for a ventilator patient. In one example, the weight based dosages for each drug as identified in step 301 is used to determine if the dosage of each drug meets the defined dosage preferences. Bolus doses may also be analyzed to determine if the patient is being over medicated.

A dosage ratio may be calculated based on the weight based dosages of the sedative and pain therapy medications. In one example, the ratio defines a relationship between the amount (dosage) of a sedative administered to a patient and the amount (dosage) of a pain therapy drug administered to the patient. The calculated dosage ratio is then compared to the preferred dosage ratio as defined by the rules and protocols to determine if there is a variance between the calculated dosage ratio and the preferred dosage ratio.

In step 304, it is determined if the dosage of drugs administered is within a pre-define limit. For example, information regarding limits (e.g., soft or hard limits) for one or more drugs may be accessed and compared to the dosages for each drug to determine if the dosages are within the limits for that drug.

In step 305, infusion analytics are generated according to the determinations in step 302, 303 and 304.

Figure 4:
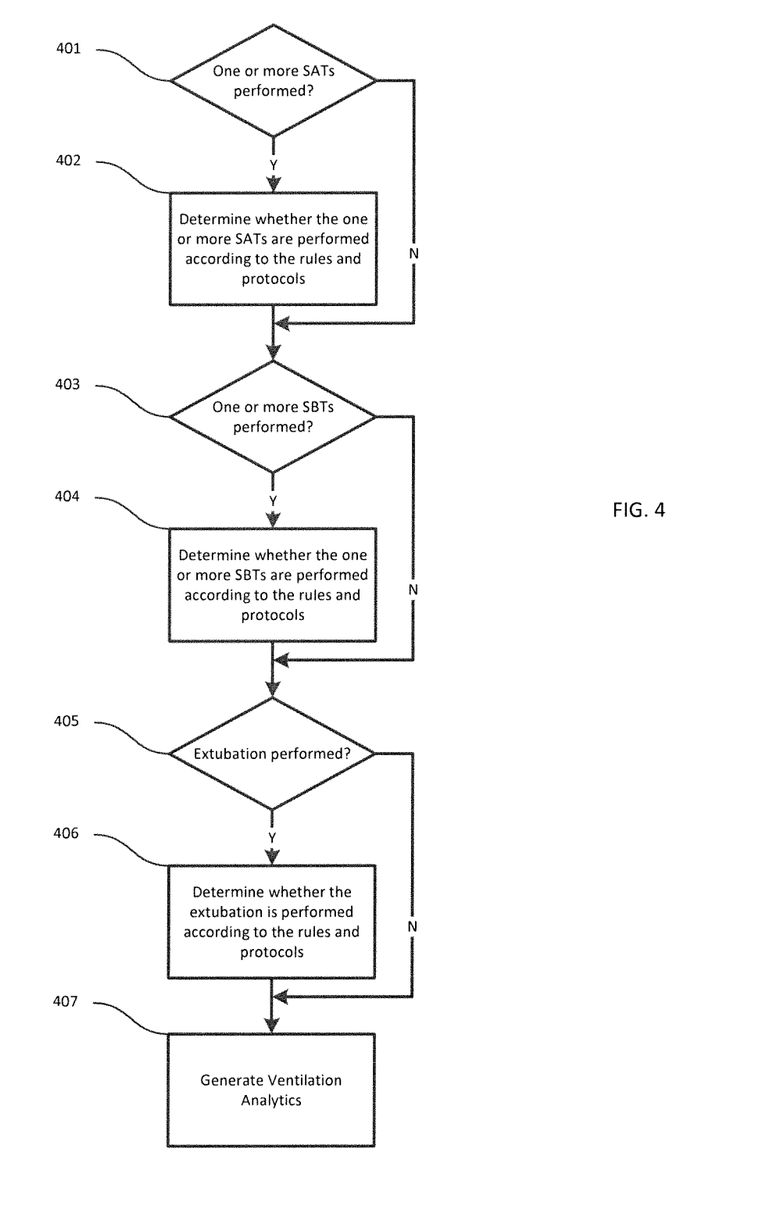
FIG. 4 illustrates an example process for generating example ventilation analytics for a ventilated patient.

FIG. 4 illustrates an example process 400 for generating example ventilation analytics for a ventilated patient.

In step 401 it is determined whether one or more SATs were performed with respect to the patient. In order to perform SATs or sedation vacations, the dosage of sedation and pain therapy medication administrated to a patient is typically reduced (e.g., to a lower dosage or stopped). In step 401, dosage information and infusion starts and stops provided by the infusion pump 101 to the coordinated engine 106 and knowledge portal 111 are analyzed to identify SATs. That is, changes in dosage and/or start/stop of dosage are analyzed and where the dosage is reduced to a level that indicates an SAT (e.g., reduced or stopped), a marker is generated indicating a start of an SAT. The dosages following the marker are then analyzed until an increase in dosage to a level indicating a termination of an SAT is observed (e.g., an increase or restart). Another marker is then generated indicating a termination of the SAT. Instead of a dosage increase, indicating a termination of an SAT, in some instances an SAT may be followed by an SBT. In such instances, a marker may be generated once an SBT is initiated, to indicate the termination of an SAT.

If, in step 401, one or more SATs are identified, in step 402, is determined whether the SATs are performed according to the rules and protocols. For example, the rules and protocols may define preferred timing, frequency and/or duration of SATs. For example, the rules and protocols may define that SATs should be performed one or more times per day and/or preferred times for conducting SATs. The markers for the SATs are used to determine the frequency of the SATs and/or the timing for each SAT performed. The determined frequency and/or timing is then compared to the frequency and/or timing defined by the rules to determine if there is a variance between the frequency and/or timing actual of the performed SATs and the preferred frequency and/or timing of SATs.

Furthermore, the rules and protocols may define a preferred duration. The start/end markers for each SAT may be used to determine the duration of the SAT. The duration is then compared to the defined preferred duration. In one example, the preferred duration indicates that an SAT was successful. If, in step 401, no SATs are identified, the process continues to step 403.

In step 403, it is determined whether one or more SBTs were performed with respect to the patient. When performing an SBT, the ventilator 103 is put into a different mode in order to perform the SBT. The mode information provided by the ventilator 103 is analyzed to determine when a change in mode indicative of an SBT occurs. A marker is generated when such a change is detected, marking the beginning of the SBT. Next, ventilator information is analyzed to identify a termination of the SBT. A termination of an SBT may be indicated by a change in the mode of the ventilator 103 or by the termination of ventilation indicative of an extubation. A marker is generated when an SBT termination is identified.

If, in step 403, one or more SBTs are identified, in step 404, it is determined whether the SBTs are performed according to the rules and protocols. In one example, the rules and protocols may include rules regarding preferred timing, frequency and/or duration of SATs. Furthermore, the rules may indicate one or more prerequisites before the SBT is performed.

For example, the rules may define that once it is determined that a patient is a good candidate for a SBT (e.g., a candidate for weaning), an SAT should be performed and after a predefined amount of time an SBT should be initiated. The markers for the SBT are used to determine the timing and duration of the SBT. Furthermore, the marker for the preceding SAT is used to determine the amount of time before an SBT is initiated following the SAT, and whether the SBT is successfully completed.

The rules and protocols may also define a preferred duration for an SBT. The start/end markers for each SBT may be used to determine the duration of the SBT. The duration is then compared to the defined preferred duration. In one example, the preferred duration indicates that an SBT was successful.

Furthermore, a successful SBT (e.g., defined by a specific duration) in patients that are a good candidate for weaning should be followed by an extubation within a predefined amount of time of the SBT being initiated. The markers are used along with markers indicating an extubation to determine a time elapsed between a successful SBT and extubation in certain patients.

The information is then compared to the SBT rules and protocols to determine if there is a variance between the timing, duration and prerequisite of actual SBTs performed and the preferred timing, duration and prerequisite of SBTs. If, in step 403, no SATs are identified, the process continues to step 405.

In step 405, it is determined whether an extubation of the patient was performed. An extubation may be identified if a termination in ventilation information is detected (e.g., following a successful SBT). In one example, in response to detecting a termination of ventilation information, a marker is generated indicating an extubation. In one example, a threshold time may be defined before a termination of ventilation is interpreted as an extubation. The threshold time may, for example, account for switching the patient to a remote ventilator for various reasons.

If, in step 405, it is determined that an extubation was performed with respect to the patient, in step 406 it is determined if the extubation was performed according to the rules and protocols. For example, the rules and protocols may define a timing for performing an extubation following a successful SBT being performed. The markers for SBTs and the extubation may be used to determine if an SBT was successfully completed and the time lapsed after the successful SBT (e.g., as defined by a specific duration), before extubation was performed. This information is then compared to the rules and protocols to determine if there is a variance between the timing and preceding events of the extubation and the defined rules and protocols for extubation.

In step 407, ventilation analytics are generated according to the determinations in steps 401-406.

Accordingly, the embodiments of the disclosed system and methods provide for processing information from one or more infusion pumps, ventilators, hospital information systems, monitors, dispensing systems, and/or laboratory systems providing information regarding a ventilated patient and analyzing the information to assess protocol and best practices compliance. The collected information can be processed to generate various markers and/or analytics that provide insight into the clinical intervention events and how the timing/pattern of these events affects the weaning process and facilitate a complete view of the weaning process, including sedation/pain therapy, SATs, SBTs and extubation, thus, driving better cross-functional team work between physicians, nursing and respiratory technicians. Measuring and driving compliance may enable clinicians to measurably optimize and improve the weaning of ventilated patients. Furthermore, the generated markers and analytics may help provide.

Figure 5:
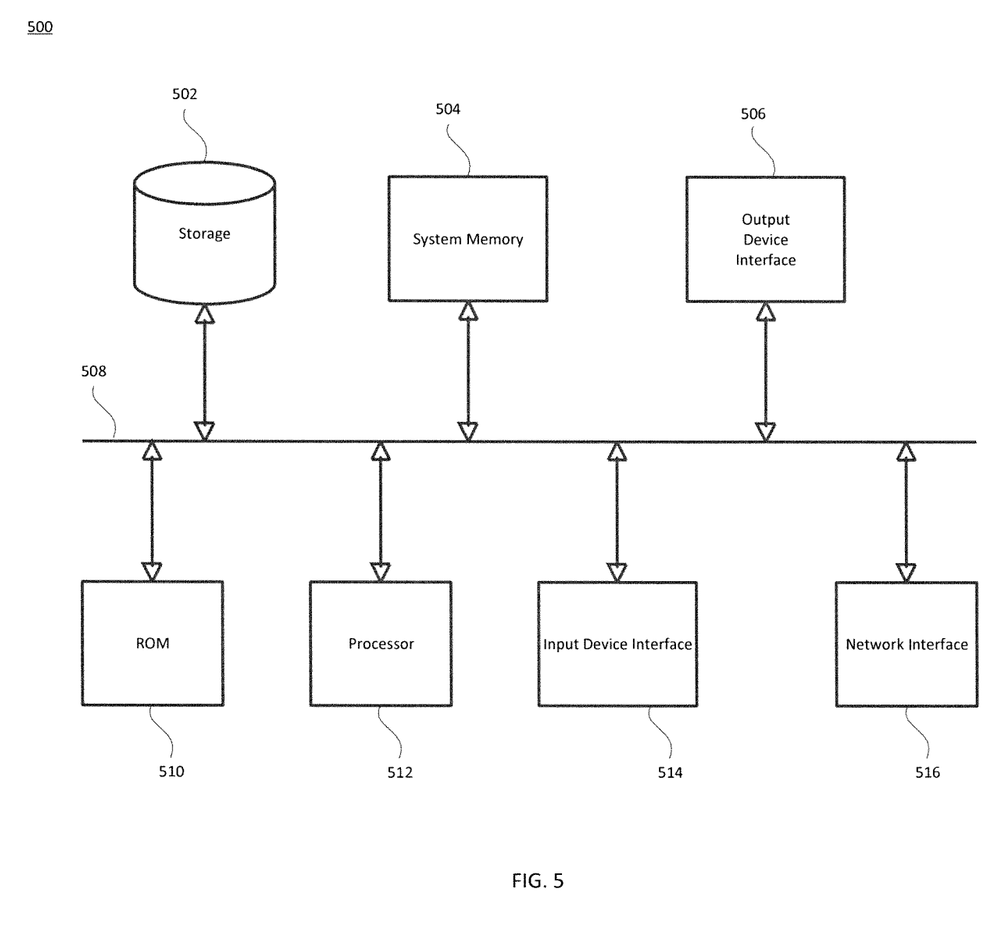
FIG. 5 conceptually illustrates an electronic system with which some implementations of the subject technology are implemented.

FIG. 5 conceptually illustrates an electronic system with which some implementations of the subject technology are implemented. Electronic system 500 can be a server, computer, phone. PDA, laptop, tablet computer, television with one or more processors embedded therein or coupled thereto, or any other sort of electronic device. Such an electronic system includes various types of computer readable media and interfaces for various other types of computer readable media. Electronic system 500 includes a bus 508, processing unit(s) 512, a system memory 504, a read-only memory (ROM) 510, a permanent storage device 502, an input device interface 514, an output device interface 506, and a network interface 516.

Bus 508 collectively represents all system, peripheral, and chipset buses that communicatively connect the numerous internal devices of electronic system 500. For instance, bus 508 communicatively connects processing unit(s) 512 with ROM 510, system memory 504, and permanent storage device 502.

From these various memory units, processing unit(s) 512 retrieves instructions to execute and data to process in order to execute the processes of the subject disclosure. The processing unit(s) can be a single processor or a multi-core processor in different implementations.

ROM 510 stores static data and instructions that are needed by processing unit(s) 512 and other modules of the electronic system. Permanent storage device 502, on the other hand, is a read-and-write memory device. This device is a non-volatile memory unit that stores instructions and data even when electronic system 500 is off. Some implementations of the subject disclosure use a mass-storage device (such as a magnetic or optical disk and its corresponding disk drive) as permanent storage device 502.

Other implementations use a removable storage device (such as a floppy disk, flash drive, and its corresponding disk drive) as permanent storage device 502. Like permanent storage device 502, system memory 504 is a read-and-write memory device. However, unlike storage device 502, system memory 504 is a volatile read-and-write memory, such a random access memory. System memory 504 stores some of the instructions and data that the processor needs at runtime. In some implementations, the processes of the subject disclosure are stored in system memory 504, permanent storage device 502, and/or ROM 510. For example, the various memory units include instructions for determining compliance with one or more patient care rules and protocols according to various implementations. From these various memory units, processing unit(s) 512 retrieves instructions to execute and data to process in order to execute the processes of some implementations.

Bus 508 also connects to input and output device interfaces 514 and 506. Input device interface 514 enables the user to communicate information and select commands to the electronic system. Input devices used with input device interface 514 include, for example, alphanumeric keyboards and pointing devices (also called "cursor control devices"). Output device interfaces 506 enables, for example, the display of images generated by the electronic system 500. Output devices used with output device interface 506 include, for example, printers and display devices, such as cathode ray tubes (CRT) or liquid crystal displays (LCD). Some implementations include devices such as a touchscreen that functions as both input and output devices.

Finally, as shown in FIG. 5, bus 508 also couples electronic system 500 to a network (not shown) through a network interface 516. In this manner, the computer can be a part of a network of computers (such as a local area network ("LAN"), a wide area network ("WAN"), or an Intranet, or a network of networks, such as the Internet. Any or all components of electronic system 500 can be used in conjunction with the subject disclosure.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

In the previous detailed description, numerous specific details have been set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A method comprising:
   administering, by an infusion pump, one or more drugs to a patient, the one or more drugs including at least one of a sedative drug and a pain therapy drug;
   receiving, from the infusion pump by a processor without user interaction, infusion information pertaining to one or more drugs being administered to the patient by the infusion pump;
   receiving, while the infusion pump is administering the one or more drugs to the patient, from a ventilator by the processor without user interaction, ventilation information pertaining to ventilation being provided to the patient by the ventilator;
   reducing a dosage of at least one of the one or more drugs administered to the patient;
   determining, in real time by the processor, based on the reduction of the dosage, a spontaneous awakening trial ("SAT") comprising a first period of time in which the ventilation is provided while the dosage of the one or more drugs administered to the patient by the infusion pump is reduced or stopped;
   changing an operation mode of the ventilator while the ventilator is providing the ventilation to the patient and the one or more drugs are being administered to the patient to initiate a spontaneous breathing trial ("SBT") comprising a second period of time in which the ventilation provided to the patient is adjusted;
   determining, in real time by the processor, based on the change of the operation mode of the ventilator, that the SBT occurred;
   detecting, in real time by the processor, that the dosage reduced or stopped while the one or more drugs are being administered to the patient, and the change to the operation mode of the ventilator while the patient is being ventilated;
   generating, based on detecting that the dosage reduced or stopped, a first plurality of markers indicating a start and a termination of the SAT;
   generating, based on detecting the change to the operation mode, a second plurality of markers indicating a start and a termination of the SBT;
   accessing, from a hospital network including a hospital information system, a set of rules and protocols associated with care of the patient;
   determining, in real time by the processor based on the ventilation information and the infusion information, a variation between actual care of the patient, including the one or more drugs administered to the patient and the ventilation provided to the patient, and the set of rules and protocols associated with care of the patient;
   determining, in real time by the processor, based on the generated first or second plurality of markers and determining the variation, a first indication of whether to initiate termination of the ventilation and a timing for performing an extubation of the patient ventilation;
   providing, by the processor, to a client device associated with a care provider in real time responsive to determining the first indication, the first indication of whether to initiate termination of the ventilation and the timing for performing the extubation;
   terminating the ventilation of the patient;
   determining whether the ventilation was terminated for a threshold period of time;
   responsive to the ventilation being terminated for a threshold period of time:
      determining that the extubation of the patient was performed;
      determining whether the timing of the extubation of the patient was performed according to the rules and protocols;
      recording an extubation marker representative of the extubation; and
      providing, to the client device for display at the client device, a warning notification responsive to determining the variation, and a notification of whether the timing of the extubation was performed according to the rules and procedures,
   wherein the client device is remotely connected to the infusion pump and the ventilator over a network.

2. The method of claim 1, further comprising:
   in response to determining that the SAT has occurred, determining a start time and a stop time of the SAT based at least in part on one or more of the infusion information and ventilation information.

3. The method of claim 1, further comprising:
in response to determining that the SAT has occurred, comparing a frequency of the SAT to a preferred frequency of SATs defined by the set of rules and protocols.

4. The method of claim 1, further comprising:
in response to determining that the SAT has occurred, determining whether each of the SAT were successful based on a duration of the SAT, wherein the duration of the SAT is determined based on a start time and a stop time of the SAT.

5. The method of claim 1, further comprising:
in response to determining that the SBT has occurred, determining a start time and a stop time of the SBT based at least in part on
one or more of the infusion information and ventilation information.

6. The method of claim 1, further comprising:
in response to determining that the SBT has occurred, determining whether each of the SBT was successful based on a duration of the SBT, wherein the duration of the SBT is determined based on a start time and a stop time of the SBT.

7. The method of claim 1, further comprising:
in response to determining that the SBT has occurred, identifying one or more preceding events that occurred previous to the SBT and comparing the one more preceding events to one or more preferred preceding events defined by the set of rules and protocols.

8. The method of claim 1, further comprising:
in response to determining that the extubation was performed, identifying one or more preceding events that occurred previous to the extubation and comparing the one or more preceding events to one or more preferred preceding events defined by the set of rules and protocols.

9. The method of claim 1, further comprising:
receiving patient vital signs indicating vital conditions of the patient from one or more of a laboratory system, a monitor, or dispensing system by the processor; and wherein determining the variation is further based on the patient vital signs.

10. The method of claim 1, further comprising:
receiving ADT information including one or more of demographic information and state information for the patient from a hospital information system by the processor; and wherein determining the variation is further based on the ADT information.

11. The method of claim 1, further comprising the steps of:
receiving information from at least one of a laboratory system, dispensing system or a monitor by the processor, and wherein the determination of the variation is further based, at least in part, on the information from the at least one of the laboratory system, dispensing system or the monitor.

12. The method of claim 1, wherein the infusion information includes one or more of a drug type for each drug administered to the patient, a dosage of each drug administered to the patient, a rate of each drug administered to the patient, or an indication of infusion started or stopped.

13. The method of claim 1, wherein the ventilation information includes one or more of a respiratory rate, tidal volume, amount of oxygen, amount of peek respiratory pressure, or alarms triggered at the ventilator.

14. The method of claim 1, further comprising the steps of:
calculating a weight based dosage of each drug administered to the patient by the infusion pump based at least in part on the infusion information and a weight of the patient provided by an information system, wherein the set of rules and protocols includes a preferred dosage for each drug administered to the patient; and
comparing the weight based dosage of each drug to the preferred dosage for the drug.

15. The method of claim 1, wherein the drugs administered to the patient includes at least a sedative and an analgesic.

16. The method of claim 15, further comprising the steps of:
calculating a weight based dosage of each of the sedative and analgesic administered to the patient based at least in part on the infusion information and a weight of the patient;
calculating a ratio of sedative to analgesic based on the weight based dosage of each of the sedative and analgesic, wherein the set of rules and protocols includes a preferred ratio of sedative to analgesic; and
comparing the ratio of sedative to analgesics to the preferred ratio of sedative and analgesics.

17. The method of claim 1, further comprising the steps of:
identifying the set of rules and protocols, wherein the set of rules and protocols include preferences regarding the drugs administered to the patient and a weaning process followed with regards to the patient.

18. The method of claim 1, wherein determining the variation comprises:
identifying, from the rules and procedures, the timing for performing the extubation following a successful SBT being performed; and
determining that a successful SBT was completed and that the timing for performing the extubation lapsed after the successful SBT before the extubation was performed.

19. A system, comprising:
an infusion pump administering one or more drugs to a patient, and providing, without user interaction, infusion information pertaining to the one or more drugs being administered to the patient, the infusion pump reducing a dosage of at least one of the one or more drugs administered to the patient during a first period of time;
a ventilator providing ventilation to the patient, and providing, without user interaction, ventilation information pertaining to the ventilation provided to the patient by the ventilator, an operation mode of the ventilator being changed while the ventilator is providing the ventilation to the patient and the one or more drugs are being administered to the patient; and
a computing device communicably coupled to the infusion pump and the ventilator, the computing device comprising one or more processing units and a memory, the memory including instructions stored thereon that, when executed, cause the computing device to perform operations in real time, comprising:
receiving, while the infusion pump is administering the one or more drugs to the patient, the infusion information and the ventilation information;
determining a set of rules and protocols associated with care of the patient, at least in part based on the received infusion information and the received ventilation information;

determining, based on the reduction of the dosage by the infusion pump, a spontaneous awakening trial ("SAT") comprising a first period of time in which the ventilation is provided while the dosage of the one or more drugs administered to the patient by the infusion pump is reduced or stopped;

determining, based on the change of the operation mode of the ventilator, a spontaneous breathing trial ("SBT") comprising a second period of time in which the ventilation provided to the patient is adjusted has occurred;

detecting, based on the received infusion information and the received ventilation information, the change in the dosage of the drugs being administered to the patient, and the change to the operation mode of the ventilator while the patient is being ventilated;

generating, based on detecting the change in the dosage, a first plurality of markers indicating a start and a termination of the SAT;

generating, based on detecting the change to the operation mode, a second plurality of markers indicating a start and a termination of the SBT;

determining, based at least on the generated first or second plurality of markers, a deviation from the set of rules or protocols and whether to initiate termination of the ventilation and a timing for performing an extubation of the patient ventilation;

facilitating termination of the ventilation;

determining whether the ventilation was terminated for a threshold period of time; and responsive to the ventilation being terminated for a threshold period of time:
 determining that the extubation of the patient was performed;
 determining whether the timing of the extubation of the patient was performed according to the rules and protocols;
 recording an extubation marker representative of the extubation; and
 providing, to a client device remotely connected to the ventilator and the infusion pump over a network, a warning notification responsive to determining the deviation, and a notification of whether the timing of the extubation was performed according to the rules and procedures.

20. The system of claim 19, wherein:
the infusion pump is coupled to an infusion system manager configured to receive infusion messages from the infusion pump and generate the infusion information provided to the computing device.

21. The system of claim 19, further comprising:
one or more of a laboratory system, a vital signs monitor, or a dispensing system; and
wherein the computing device is configured to determine analytics based on a variation further based at least in part on information provided by at least one of the laboratory system, vital signs monitor or the dispensing system.

22. A non-transitory computer-readable medium having computer-executable instructions stored thereon for execution by a processor to perform a method, the method comprising the steps of:

administering, by an infusion pump, one or more drugs to a patient, the one or more drugs including at least one of a sedative drug and a pain therapy drug;

receiving, from the infusion pump without user interaction, infusion information pertaining to one or more drugs being administered to the patient by the infusion pump, the one or more drugs including sedatives and pain therapy drugs, the infusion pump reducing a dosage of at least one of the one or more drugs administered to the patient during a first period of time;

receiving, while the infusion pump is administering the one or more drugs to the patient, from a ventilator without user interaction, ventilation information pertaining to ventilation being provided to the patient by the ventilator, an operation mode of the ventilator being changed while the ventilator is providing the ventilation to the patient and the one or more drugs are being administered to the patient;

determining, in real time, based on the reduction of the dosage by the infusion pump, a spontaneous awakening trial ("SAT") comprising a first period of time in which the ventilation is provided while the dosage of the one or more drugs administered to the patient by the infusion pump is reduced or stopped;

determining, based on the change of the operation mode of the ventilator, a spontaneous breathing trial ("SBT") comprising a second period of time in which the ventilation provided to the patient is adjusted has occurred;

calculating a weight based dosage of each of the sedative and pain therapy drugs administered to the patient based at least in part on the infusion information and a weight of the patient;

calculating a ratio of sedative to pain therapy drugs based on the weight based dosage of each of the sedative and pain therapy drugs;

providing, in real time, one or more analytics for display at a client device remotely connected to the ventilator and the infusion pump over a network, wherein the one or more analytics provide indications of a variation between actual care of the patient, including the one or more drugs administered to the patient and the ventilation provided to the patient, and a set of rules and protocols associated with care of the patient, wherein the set of rules and protocols is accessed from a hospital network including a hospital information system and includes a preferred ratio of sedative to pain therapy drugs and the one or more analytics comprises a comparison of the ratio of sedative to pain to the preferred ratio of sedative to pain; and providing, to the client device in real time, one or more indicators of when to initiate termination of the ventilation, including a timing for performing an extubation of the patient ventilation, based at least on the one or more analytics and whether one or more SATs and one or more SBTs have occurred;

generating, based a detected change in the dosage, one or more markers indicating a start or a termination of the SAT;

generating, based on detecting the change to the operation mode, one or more second markers indicating a start or a termination of the SBT;

determining, based at least on the generated first or second markers, a deviation from the set of rules or protocols;

facilitating termination of the ventilation;

determining whether the ventilation was terminated for a threshold period of time; and responsive to the ventilation being terminated for a threshold period of time:
 determining that the extubation of the patient was performed;

determining whether the timing of the extubation of the patient was performed according to the rules and protocols;

recording an extubation marker representative of the extubation; and providing a warning notification to the client device in real time responsive to determining the deviation, and a notification of whether the timing of the extubation was performed according to the rules and procedures.

* * * * *